US00PP21598P2

(12) United States Plant Patent
Hanes

(10) Patent No.: US PP21,598 P2
(45) Date of Patent: Dec. 28, 2010

(54) ***PETUNIA* PLANT NAMED 'PIC REDDA'**

(50) Latin Name: *Petunia hybrida*
Varietal Denomination: Pic Redda

(75) Inventor: Mitchell Hanes, Morgan Hill, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/653,295

(22) Filed: Dec. 11, 2009

(51) Int. Cl.
*A01H 5/00* (2006.01)

(52) U.S. Cl. ..... Plt./356

(58) Field of Classification Search ..... Plt./356
See application file for complete search history.

*Primary Examiner*—Kent L Bell
(74) *Attorney, Agent, or Firm*—S. Matthew Edwards

(57) ABSTRACT

A new *Petunia* plant named 'Pic Redda' particularly distinguished by the new cultivar has small bold red flowers, good floriferousness, medium green foliage, initially semi-compact and then an outwardly spreading plant habit.

1 Drawing Sheet

Latin name of the genus and species of the plant claimed: *Petunia hybrida.*

Varietal denomination: 'Pic Redda'.

BACKGROUND OF THE NEW PLANT

The present invention comprises a new *Petunia,* botanically known as *Petunia hybrida,* and hereinafter referred to by the variety name 'Pic Redda.'

'Pic Redda' is a product of a planned breeding program. The new cultivar has small bold red flowers, good floriferousness, medium green foliage, initially semi-compact and then an outwardly spreading plant habit.

'Pic Redda' originated from a hybridization made in June 2004 in a controlled breeding environment in Gilroy, Calif. The female parent was the proprietary, unpatented plant designated '1393-1,' with small red flowers, and a more upright habit.

The male parent of 'Pic Redda' is a commercially available variety identified as 'MP101,' U.S. Plant Pat. No. 14,998, with a lighter red colored flower and lighter colored and larger foliage.

'Pic Redda' was selected as one flowering plant within the progeny of the stated cross in the May 2005 in a controlled environment in Gilroy, Calif.

The first act of asexual reproduction of 'Pic Redda' was accomplished when vegetative cuttings were propagated from the initial selection in May 2005, in a controlled environment in Gilroy, Calif.

BRIEF SUMMARY OF INVENTION

Horticultural examination of plants grown from cuttings of the plant initiated in May 2005, and continuing thereafter, has demonstrated that the combination of characteristics as herein disclosed for 'Pic Redda' are firmly fixed and are retained through successive generations of asexual reproduction.

'Pic Redda' has not been observed under all possible environmental conditions. The phenotype may vary significantly with variations in environment such as temperature, light intensity and day length.

A Plant Breeder's Right for this cultivar was applied for in Canada on Jan. 30, 2009. 'Pic Redda' has not been made publicly available more than one year prior to the filing of this application.

The following traits have been repeatedly observed and are determined to be basic characteristics of the new variety. The combination of these characteristics distinguishes this Petunia as a new and distinct variety.

BRIEF DESCRIPTION OF THE PHOTOGRAPHS

Figure 1:
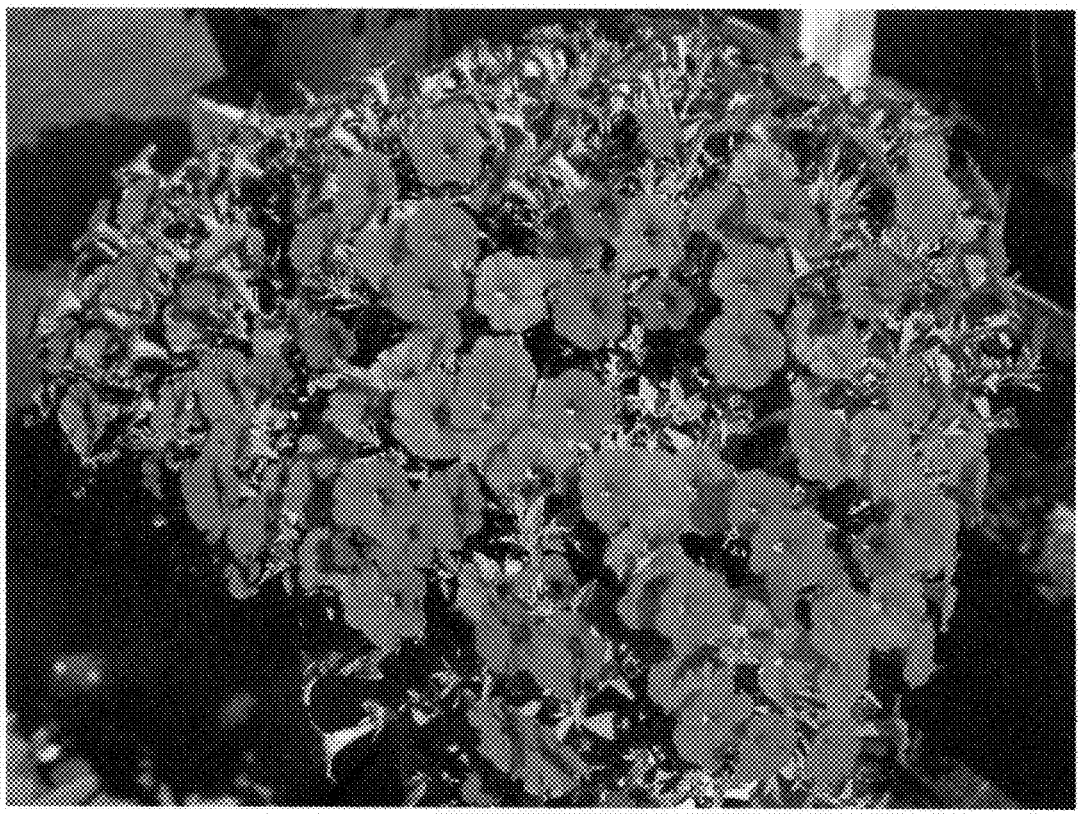
Figure 2:
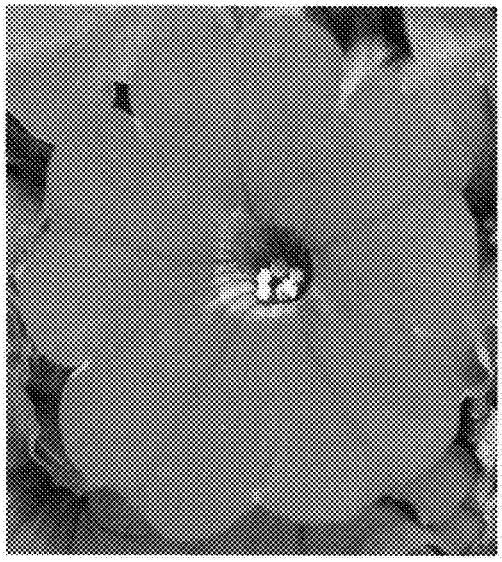

The accompanying photographic drawing shows typical flower and foliage characteristics of 'Pic Redda' with colors being as true as possible with an illustration of this type. The photographic drawing shows in FIG. 1, three flowering potted plants of the new variety, and a close-up of the flowers in FIG. 2.

DETAILED BOTANICAL DESCRIPTION

The plant descriptions, measurements and aforementioned photographs were taken in Gilroy, Calif. from plants growing outside in 10 inch basket trials, 3 plants per basket. These plants were approximately 12 weeks of age.

Color references are made to The Royal Horticultural Society Colour Chart (R.H.S.) 2001.

TABLE 1

DIFFERENCES BETWEEN THE NEW VARIETY 'PIC REDDA' AND THE MOST RESEMBLING VARIETY 'MP101' (U.S. Plant Pat. No. 14,998)

| | 'Pic Redda' | 'MP101' (U.S. Plant Pat. No. 14,998) |
|---|---|---|
| Foliage color: | Darker | Lighter |
| Foliage size: | Smaller | Larger |
| Flower color: | Slightly darker | Slightly lighter, more red |

Plant:

*Form, growth and habit.*—Initially semi-compact to outwardly spreading, strong vigorous habit, well branched, small foliage, and continuously flowering.

*Plant height.*—15-18 cm.

*Plant height* (*inflorescence included*).—19-20 cm.
*Plant width.*—35 cm.
*Garden performance and tolerance to weather.*—Very good.
*Crop time to flowering.*—About 8-9 weeks.

Roots:
Number of days to initiate roots and produce a rooted cutting.—18-23 days at about 22 degrees C.
*Type.*—Fine, fibrous, free branching.
*Color.*—RHS N155B but whiter.

Foliage:
*Arrangement.*—Alternate, upper leaves sub-opposite.
*Immature, leaf color, upper surface.*—Closest to RHS 146C with slightly RHS 146D blotching.
*Lower surface.*—Closest to RHS 146C.
*Mature, leaf color, upper surface.*—RHS 146B with RHS 146C blotching.
*Lower surface.*—Closest to RHS 146C.
*Length.*—2.0-2.2 cm.
*Width.*—1.3-1.4 cm.
*Shape.*—Ovate.
*Base shape.*—Attenuate.
*Apex shape.*—Acute.
*Margin.*—Entire.
*Texture, upper surface.*—Glandular hairs of various lengths.
*Lower surface.*—Glandular hairs of various lengths.
*Color of veins, upper surface.*—RHS 146D.
*Color of veins, lower surface.*—RHS 146D.
*Petiole color.*—RHS 146D.
*Length.*—0.2 cm.
*Diameter.*—0.20 cm.
*Texture.*—Glandular hairs of various lengths.

Stems:
*Color of stem.*—Closest to RHS 146C.
*Length of stem.*—About 20-25 cm.
*Diameter.*—0.3 cm.
*Length of internodes.*—1.0-1.3 cm.
*Texture.*—Glandular hairs.
*Color of peduncle.*—Between RHS 146B and RHS 146C.
*Length of peduncle.*—2.1-2.6 cm.
*Peduncle diameter.*—0.15 cm.
*Texture.*—Glandular hairs.

Inflorescence:
*Type.*—Flowers appear solitary in upper leaf axis. Floret type: Funnel-shaped; 5 lobed petals; fused at the base; calyx, 5 deeply lobed sepals.
*Blooming habit.*—Continuous throughout the growing season. Good floriferousness.
*Quantity of inflorescences per plant.*—About 40-50.
*Lastingness of individual blooms on the plant.*—5-7 days.
*Fragrance.*—None.

BUD (just before opening/showing color):
*Color.*—Closest to RHS 183A.
*Length.*—2.0-3.0 cm.
*Width.*—0.4-0.5 cm.
*Shape.*—Oblong.

Immature inflorescence:
*Diameter.*—2.7-3.1 cm.
*Color, upper surface.*—Closest to RHS 46A but with deeper hues and more velvety looking.
*Lower surface.*—Closest to RHS 184B.

Mature inflorescence:
*Floret horizontal diameter.*—3.5-3.7 cm.
*Vertical depth.*—4.0-4.3 cm.
*Petal color, upper surface.*—Between RHS 46A and RHS 46B; maturing with a little more blueish-red coloring.
*Lower surface.*—RHS 53D.
*Petal apex shape.*—Retuse to emarginate.
*Petal base shape.*—Fused.
*Petal margin.*—Entire.
*Waviness of petals.*—Moderate.
*Petal lobation.*—Moderate.
*Petal texture, upper surface.*—Papillose.
*Under surface.*—Few glandular hairs mainly on the veins.
*Corolla tube color inside.*—RHS N155C to RHS 155D with RHS 184A veining and RHS 183 mid-vein.
*Outside.*—RHS 164D but lighter with RHS 178B veining and RHS 144B mid-vein.
*Corolla tube length.*—12.5-2.7 cm.
*Corolla texture.*—Long glandular hairs on the outside.

Calyx:
*Color, upper surface.*—RHS 146C.
*Lower surface.*—RHS 146B.
*Length.*—0.9-1.1 cm.
*Width.*—0.15 cm.
*Shape.*—Narrowly oblong.
*Apex shape.*—Obtuse.
*Based.*—Fused.
*Margins.*—Entire.
*Texture, upper surface.*—Glandular hairs.
*Lower surface.*—Glandular hairs.

Reproductive organs:
*Pistil.*—1.
*Length.*—2.1 cm.
*Style color.*—RHS 145C.
*Style length.*—1.9-2.0 cm.
*Stigma color.*—RHS 145A.
*Ovary color.*—RHS 144B.
*Stamens.*—5.
*Color of filaments.*—RHS 155B with RHS 53D at the anther.
*Length filaments.*—0.6-2.0 cm.
*Anther color.*—RHS 155B.
*Anther length.*—About 0.2 cm.
*Anther shape.*—Reniform.
*Color of pollen.*—RHS 158C.
*Pollen amount.*—Moderate.
*Fertility/seed set.*—Has not been observed on this hybrid.

Disease/pest resistance: Has not been observed on this hybrid.

What is claimed is:

1. A new and distinct variety of *Petunia* plant named 'Pic Redda,' substantially as illustrated and described herein.

* * * * *

UNITED STATES PATENT AND TRADEMARK OFFICE

CERTIFICATE OF CORRECTION

PATENT NO. : PP21,598 P2
APPLICATION NO. : 12/653295
DATED : December 28, 2010
INVENTOR(S) : Hanes It is certified that error appears in the above-identified patent and that said Letters Patent is hereby corrected as shown below:

Title page, Item (57) in the ABSTRACT, delete "the new cultivar has"

At column 4, line 22, delete "RHS 183" and insert therefor --RHS 183B--

At column 4, line 25, delete "12.5-2.7 cm" and insert therefor --2.5-2.7 cm--

Signed and Sealed this
Fifteenth Day of February, 2011

David J. Kappos

David J. Kappos
*Director of the United States Patent and Trademark Office*